(12) United States Patent
Berbee et al.

(10) Patent No.: US 9,326,668 B1
(45) Date of Patent: May 3, 2016

(54) OTOSCOPE PROVIDING IMPROVED EAR CANAL ACCESS

(71) Applicant: Wisconsin Alumni Research Foundation, Madison, WI (US)

(72) Inventors: James Berbee, Madison, WI (US); Azita Hamedani, Verona, WI (US); Greg Rebella, Hartland, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/461,103

(22) Filed: Aug. 15, 2014

(51) Int. Cl.
*A61B 1/227* (2006.01)
*A61B 1/05* (2006.01)
*A61B 1/06* (2006.01)
*A61B 1/00* (2006.01)

(52) U.S. Cl.
CPC ............. *A61B 1/227* (2013.01); *A61B 1/00032* (2013.01); *A61B 1/00052* (2013.01); *A61B 1/00112* (2013.01); *A61B 1/051* (2013.01); *A61B 1/0676* (2013.01); *A61B 1/0684* (2013.01)

(58) Field of Classification Search
CPC ...... A61B 1/227; A61B 1/051; A61B 1/0676; A61B 1/0684; A61B 1/00052; A61B 1/00032; A61B 1/00112
USPC ............... 600/184, 185, 199, 200; 709/217
See application file for complete search history.

(56) References Cited

U.S. PATENT DOCUMENTS

| | | | | | |
|---|---|---|---|---|---|
| 5,363,839 | A | * | 11/1994 | Lankford | 600/112 |
| 5,527,261 | A | * | 6/1996 | Monroe et al. | 600/109 |
| 5,682,199 | A | * | 10/1997 | Lankford | 348/72 |
| 5,762,605 | A | | 6/1998 | Cane et al. | |
| 5,919,130 | A | * | 7/1999 | Monroe et al. | 600/200 |
| 6,106,457 | A | * | 8/2000 | Perkins et al. | 600/175 |
| 6,186,944 | B1 | | 2/2001 | Tsai | |
| 6,626,825 | B2 | | 9/2003 | Tsai | |
| 8,066,634 | B2 | | 11/2011 | Andreassen et al. | |
| 2013/0271589 | A1 | * | 10/2013 | Huang | 348/77 |

\* cited by examiner

*Primary Examiner* — Pedro Philogene
*Assistant Examiner* — David C Comstock
(74) *Attorney, Agent, or Firm* — Boyle Fredrickson, S.C.

(57) ABSTRACT

An otoscope provides an extremely narrow tip holding an electronic camera sized to allow the space of the ear canal to be shared between the otoscope and a tool such as a curette for removing foreign objects. The tip may be flexible for increased patient comfort when using a compact tip design.

19 Claims, 4 Drawing Sheets

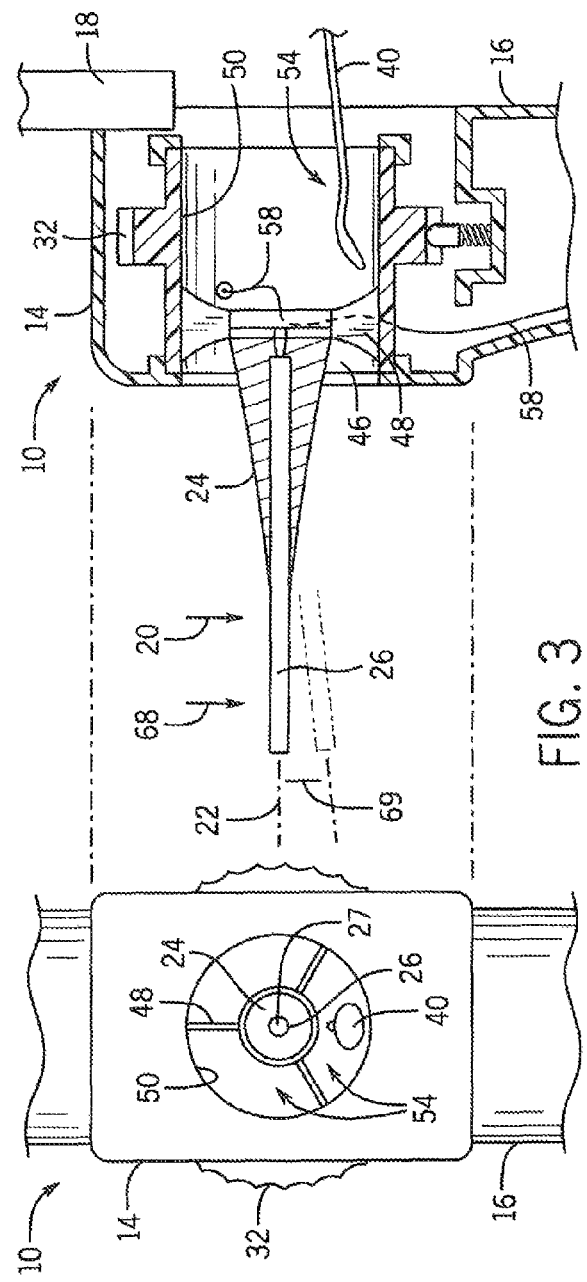
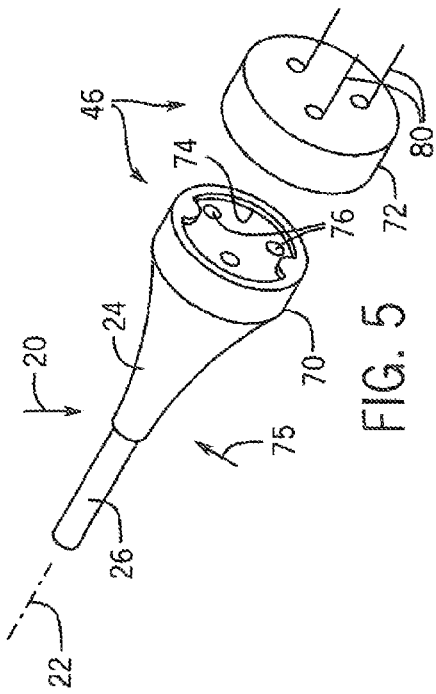
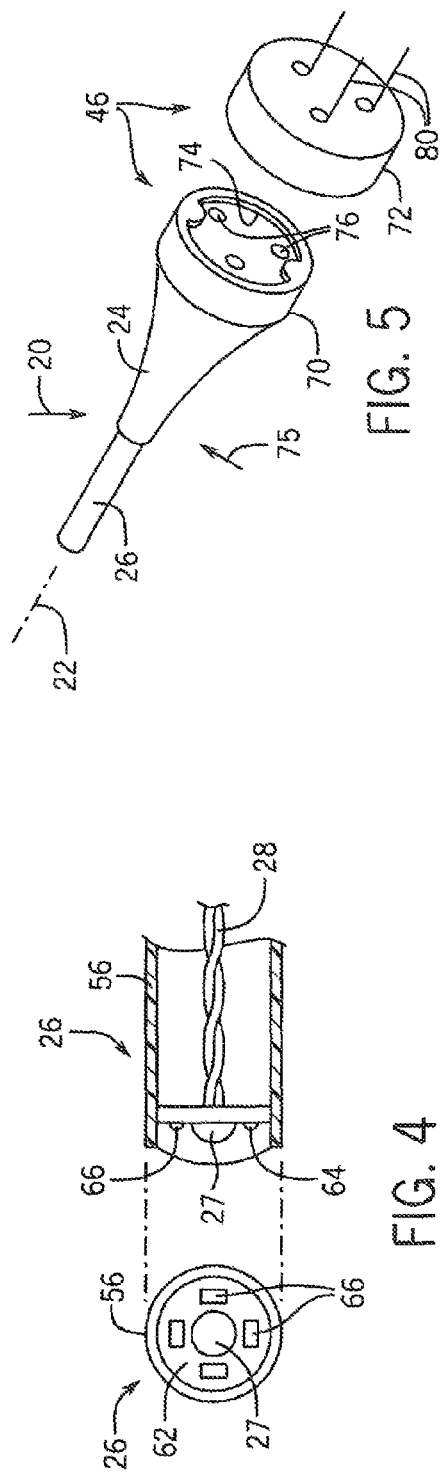

OTOSCOPE PROVIDING IMPROVED EAR CANAL ACCESS

STATEMENT REGARDING FEDERALLY SPONSORED RESEARCH OR DEVELOPMENT

CROSS REFERENCE TO RELATED APPLICATION

BACKGROUND OF THE INVENTION

The present invention relates to an otoscope for inspection of the ear and in particular to an otoscope providing improved ear canal access during inspection or during the use of additional medical instruments inserted into the car canal.

An otoscope is a medical device allowing a healthcare professional to inspect the ear canal and tympanic membrane (eardrum). A simple otoscope provides for a hollow funnel-shaped speculum whose small end is inserted into the ear canal. The funnel shape of the speculum stabilizes the otoscope against the ear canal wall and may limit the depth of insertion of the speculum. Modern otoscopes include an internal source of illumination directed down the speculum axis from a contained battery-operated lamp and may provide a magnifying lens supported outside the ear and aligned with the axis of the speculum to provide an enlarged image of the ear structure being viewed.

Recently otoscopes have been developed that include a digital camera fitting within the speculum to permit the documentation of a diagnosis by image capture.

SUMMARY OF THE INVENTION

The present invention provides an otoscope that allows improved inspection of the ear, for example, by being able to pass beyond or image to the side of minor accumulations of earwax, and which allows improved access to other medical instruments into the ear canal while the otoscope is being used, such as a curette used for the removal of earwax or foreign bodies. In this regard, the present invention may mount a digital camera on a narrow diameter, flexible support having a diameter significantly smaller than that of the ear canal. The otoscope housing provides openings that allow axial access through the otoscope body along side of the camera support when the camera support is within the ear canal. By making the camera support flexible, discomfort that may be associated with a narrow probe against the ear canal is significantly reduced.

In one embodiment, the invention may provide an otoscope having a housing with a head portion and a grip portion, the latter of which may be grasped by the hand of a healthcare professional when the head portion is in an inspection position adjacent to an outer ear of an average patient. An elongate probe element holding an electronic camera is supported by the head portion so that a distal end of the probe element may extend along an axis into the ear canal, the probe element being sized to be inserted into ear canal for inspection of the ear canal without blocking the ear canal to access by other instruments within the ear canal and passing by the probe element as so inserted.

It is thus a feature of at least one embodiment of the invention to redesign the otoscope probe so as to open a channel between the probe and the walls of the ear canal for improved imaging and access.

The probe element may include a distal portion having a maximum outside diameter less than an average diameter of the patient's ear canal for a length of at least one-half the length of the patient's ear canal.

It is thus a feature of at least one embodiment of the invention to provide a probe that can provide clearance for a second medical instrument (such as a curette) for substantially the entire length of the probe within the ear canal.

The distal portion of the probe element may be flexible to bend with contact against the ear canal.

It is thus a feature of at least one embodiment of the invention to permit the use of a small diameter probe without increased discomfort to the patient.

The probe element may provide a substantially rigid proximal portion providing less flexibility than the distal portion comprising at least one-third a length of the probe element.

It is thus a feature of at least one embodiment of the invention to permit a high degree of flexibility at the tip for comfort while preserving alignment of the probe over the necessary probe length.

The distal portion may be a flexible member extending slidably and coaxially through the substantially rigid proximal portion.

It is thus a feature of at least one embodiment of the invention to provide a probe that may be extended or retracted with respect to the housing for improved positioning after the otoscope is stabilized against the patient by the healthcare professional.

The probe element may include a breakaway electrical connector connecting flexible conductors within the probe element to circuitry within the housing, the breakaway electrical conductor providing a reversible separation of connector portions at a predetermined oblique force.

It is thus a feature of at least one embodiment of the invention to reduce the risk of damage of a slender probe during clinical use.

The head portion of the otoscope may include at least one passageway extending substantially parallel to the axis to a side of the axis allowing insertion of tools through the head portion into the ear canal when the probe portion is within the ear canal.

It is thus a feature of at least one embodiment of the invention to provide axial access to the ear canal through the otoscope when the probe is in place in the ear.

The head portion of the otoscope may support the probe element through a rotating coupling allowing rotation of the probe element about the axis with respect to the head portion.

It is thus a feature of at least one embodiment of the invention to provide a method for orienting images acquired by the camera with respect to the housing body, for example, for later viewing when those images are exported to an external device, such orientation adhering to a consistent standard.

The grip portion may extend substantially perpendicular to the axis of the probe.

It is thus a feature of at least one embodiment of the invention to provide an otoscope having a proven form factor familiar to healthcare professionals.

The head portion of the otoscope may include an electronic display communicating with the camera portion for displaying an image from the camera.

It is thus a feature of at least one embodiment of the invention to provide convenient real-time imaging of the ear in a manner that mimics a conventional otoscope both with respect placement of the display on the housing and the orientation of the display to be viewed along the normal line of sight from the healthcare professional to the structure of the ear.

The display may be displaceably mounted on the housing to be movable from covering the passageway used for instruments to uncovering the passageway.

It is thus a feature of at least one embodiment of the invention to provide a compact configuration for the otoscope that nevertheless allows axial access through the otoscope to the ear canal.

The housing may hold a battery communicating electrical power to the camera.

It is thus a feature of at least one embodiment of the invention to provide a handheld, portable, and compact device for regular clinical use.

These particular objects and advantages may apply to only some embodiments falling within the claims and thus do not define the scope of the invention.

BRIEF DESCRIPTION OF THE DRAWINGS

FIG. 3 is a rear fragmentary elevational view of the otoscope of FIG. 1 aligned with a side elevational cross-section taken along line 3-3 of FIG. 1 showing access ports for a curette or the like through the otoscope housing adjacent to the probe;

FIG. 4 is an aligned rear and side cross-sectional fragment of the tip of the probe element of FIG. 3 showing the camera element surrounded by LEDs as held in a flexible tube;

FIG. 5 is an exploded view of a magnetic coupling for holding the probe element to the otoscope housing in one embodiment;

DETAILED DESCRIPTION OF THE PREFERRED EMBODIMENT

Figure 1:
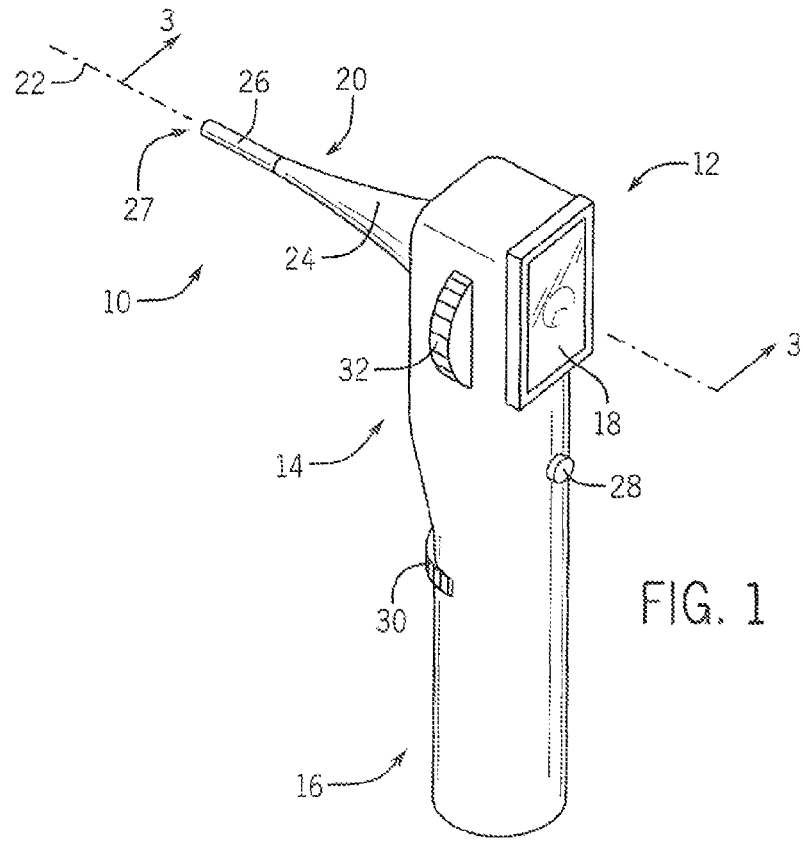
FIG. 1 is a perspective view of an otoscope constructed according to the present invention providing a housing presenting on a front side an electronic display and on a rear side having a probe element extending away from the electronic display for insertion into the ear canal.

Referring now to FIG. 1, an otoscope 10 of the present invention may provide a housing 12 having a head portion 14 and a grip portion 16. The grip portion 16 is sized to be grasped by the hand of a healthcare professional in the manner of conventional otoscope with the grip portion 16 extending generally upward from the healthcare professional's hand to the head portion 14.

A front surface of the head portion 14 may provide for an electronic display 18, for example, being a backlit three-color liquid display of a type known in the art. A probe element 20 may extend on a rear face of the head portion 14 opposite the display 18 along an axis 22 normal to the surface of the display 18. The probe element 20 may include a generally conical sheath 24 constructed of a relatively rigid thermoplastic material such as polypropylene. The conical sheath 24 may taper inward as one moves away from the head portion 14 to a distally located tip portion 26 of substantially constant diameter and constructed of a relatively flexible material such as a silicone or polyvinyl chloride material. A distal end of the tip portion 26 provides an outwardly facing camera 27 as will be discussed below. Generally the camera 27 provides an image that may be displayed on display 18.

A front side of the housing 12, at an upper end of the grip portion 16, may provide for power button 28 that may control the power to the otoscope 10, to be discussed below. In one embodiment, an extension control knob 30, also to be discussed below, may extend from a rear side of the grip portion 16 to be manipulated by the hand of the healthcare professional holding the grip portion 16. Portions of the outer periphery of a probe rotation knob 32 may extend from the right and left sides of the head portion 14 allowing rotation of the probe element 20 about the axis 22 with respect to the housing 12 as will also be discussed below.

Figure 2:
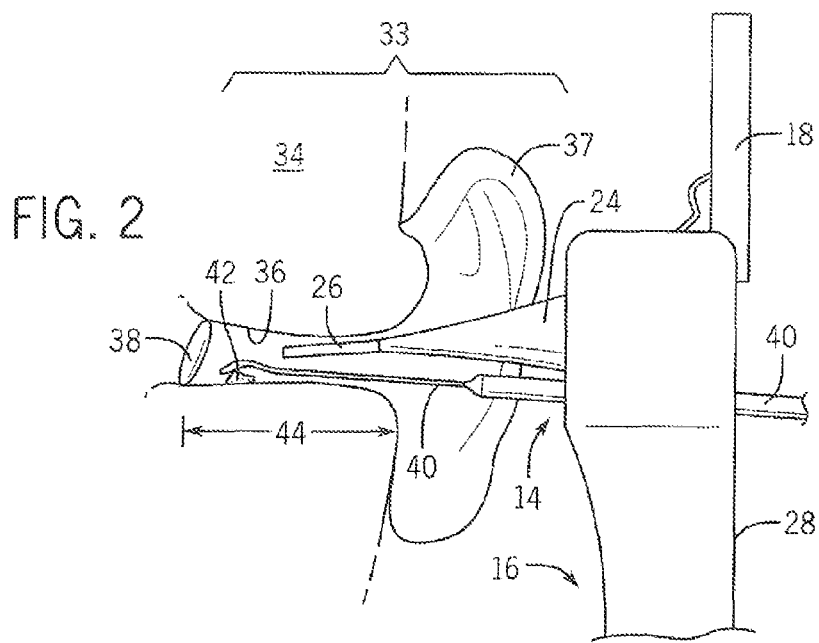
FIG. 2 is a fragmentary, side elevational view of the otoscope of FIG. 1 in place in the ear canal in an inspection position, shown in cross-section, in use for observing removal of earwax using a curette positioned adjacent to the probe element in the ear canal.

Referring now to FIG. 2, as is generally understood in the art, the outer ear 33 of a human patient 34 includes the pinna 37 providing a sound collecting structure. The pinna 37 surrounds an ear canal 36 leading to and terminating at the tympanic membrane or eardrum 38. A length 44 of the ear canal 36 in an average adult human is approximately 2.5 centimeters and the ear canal 36 has an average diameter of approximately 0.7 centimeters.

The tip portion 26 of probe element 20 of the present invention is intended to fit within the ear canal 36 to a depth so as to be able to fully image the ear canal and eardrum 38. In this regard the tip portion 26 may be sized, in one embodiment, to extend at least one centimeter into the ear canal 36 or preferably at least half the distance of the ear canal 36. More generally the tip portion 26 will be sized to extend substantially the full distance of the ear canal 36.

It is intended that the tip portion 26 be sized to allow imaging of the eardrum 38 past minor obstructions such as normally present earwax 42. The diameter of the tip portion 26 and its length are selected to allow passage within the ear canal 36 by medical instruments 40 such as a curette for removing obstructing bodies such as earwax 42 while tip portion 26 is in place for imaging. That is to permit instruments 40 to extend to the side and pass the end of the tip portion 26. In this regard, the diameter of the tip portion 26 may be less than half an average diameter of the ear canal 36 and maybe less than four millimeters and preferably smaller than 2.5 millimeters.

Referring now to FIG. 3, in one embodiment, the tip portion 26 has a length that extends rearwardly coaxially through the sheath 24 to an electrical connector assembly 46 communicating between the probe element 20 and the head portion 14 of the otoscope 10. In this way the sheath 24 may provide rigidity to the tubing of the tip portion 26 over part of its length. The connector assembly 46 may be supported by radially extending struts 48 holding the connector assembly 46 centered within and spaced away from the inner walls of a cylindrical support tube 50 that may communicate and rotate with knob 32. Rotation knob 32 thereby allows the support tube 50 to rotate with respect to the head portion 14 rotating the probe element 20 and tip portion 26 about axis 22.

This rotation allows the grip portion 16 to be angled from vertical with respect axis 22 while ensuring that an image to be generated (to be discussed below) remains intuitively aligned in the display 18 with images taken at a normal orientation with the grip portion 16 substantially vertical. In this way, captured images (as will be discussed below) may be properly interpreted without knowledge of the orientation of the grip portion 16 in a particular instance.

The struts 48 also provide for passageways 54 generally parallel to axis 22 along the side of the probe element 20 through the head portion 14 from the front face to the rear face. When these passageways 54 are to be used, the display 18 may slide upward on the head portion 14 so as to remain visible to the healthcare professional, in close proximity to the instrument 40, yet removed from obstruction of the instrument 40. When access to the passageways 54 is not required, the display 18 may slide downward over the passageways 54 to give the otoscope 10 a more compact form factor. The sheath 24 is designed to be narrower than a typical speculum to minimize interference within instrument 40 used in this regard both with respect to its distal end which is generally sized not to block the ear canal 36 and its proximal end so that the instrument 40 need not be angled so severely as to be out of alignment with the ear canal 36.

Referring now to FIG. 4, the tip portion 26 may be constructed of a flexible tube 56 that may support coaxially within the tube 56 signal and power conductors 58 leading to an integrated circuit camera 27 at the distal end of the tip portion 26. Camera 27 may be a three-color charge coupled device (CCD) of the type generally known in the art and may be supported on a substrate 62 sealed to the tube 56 by a transparent lens or encapsulation material 64. White light LEDs 66 may be attached to the substrate 62 around the camera 27 to provide a light ring of localized illumination for imaging of the ear structure. Image signals and power to the LEDs 66 are provided through the flexible conductors 58 to other circuitry of the otoscope 10. By placing the camera at the distal end of the tip portion 26, stiffening optical structures such as fiber optics may be avoided and a wide field of view may be obtained from a small diameter device without complex optics.

Referring momentarily to FIG. 3, as noted above, the present invention provides a tip portion 26 that is more flexible than the sheath 24 and more flexible than a typical otoscope speculum. Generally the flexibility of the tip portion 26 is intended to improve the comfort to the patient and reduce risk of damage to structure of the outer ear 33 caused by a small diameter probe. When the head portion 14 is stabilized, a perpendicular force 68 applied to the distal end of the tip portion 26 of 100 grams will cause a deflection 69 of no less than one millimeter. In contrast, a similar force applied to the end of the sheath 24 will provide a corresponding deflection at the end of the sheath 24 of much less than one millimeter.

Referring now to FIG. 5, the breakaway connector assembly 46 may provide for a first connector half 70, for example, having a cylindrical form as shown with a circular periphery received by a second connector half 72. The connector half 70 may provide keys 74 allowing it to attach to second connector half 72 only in a predetermined rotational orientation about axis 22. The keys 74 engage with corresponding key slots (not shown) in only one rotated position.

Connector halves 70 and 72 may be mechanically releasably retained in connection, for example, by a snap fitting, magnetic attraction or the like to be released upon receiving an oblique force 75 generally perpendicular to axis 22 that might otherwise damage the sheath 24 and/or tip portion 26, for example, if the otoscope 10 is dropped or the probe element 20 is struck against a surface inadvertently. A rear face of the connector half 70 may provide for electrical contacts 76 mating with corresponding electrical contacts 80 in the connector half 70 to provide for electrical continuity when the two are engaged.

Figure 6:
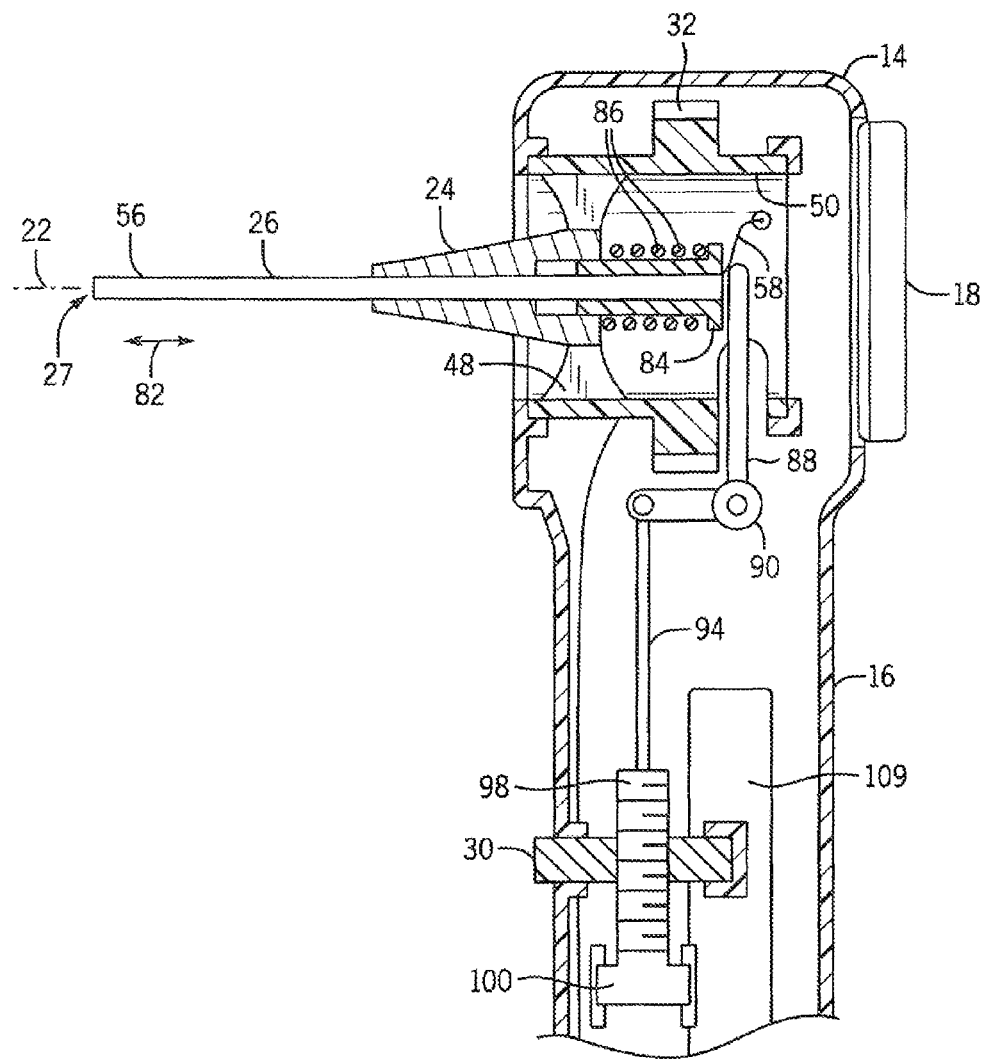
FIG. 6 is a fragmentary cross-sectional view similar to FIG. 3 showing an alternative embodiment of the otoscope allowing extension of the probe element with respect to the housing of the otoscope.

Referring now to FIG. 6, the coaxial construction of the tip portion 26 with respect to the sheath 24, allows an embodiment in which the tip portion 26 may be extended or retracted as indicated by arrow 82 along axis 22 through the hollow sheath 24. In this embodiment, the tube 56 of the tip portion 26 may slidably extend through the sheath 24 to be received within a collar 84 extending rearward from an attachment between the sheath 24 and the struts 48 (which may be a continuous structure without the breakaway connector assembly 46). The collar 84 may include key surfaces preventing its rotation with respect to the sheath 24 and may be surrounded, coaxially, by compression spring 86 urging the tip portion 26 in a forward retraction direction toward display 18. A toggle arm 88 may restrain upward motion of the collar 84 connecting between the exposed end of the collar 84, via a pivot 92, and a retractor wire 94 extending vertically downward into the grip portion 16. The retractor wire 94 is received by a threaded bar 98 fixed against rotation with respect to the housing 12 by a sliding keyway 100. Knob 30 provides a threaded bore engaging the threads of the threaded bar 98. Rotation of the knob 30 may thus be used to retract or extend the retractor wire 94 and thus retracting or extending the tip portion 26 within the sheath 24. This mechanism allows the healthcare professional to stabilize the housing 12 against the patient, for example, using the gripping hand as a stabilizing spacer between the patient's head and the housing 12, and then to adjust the tip portion 26 into or out of the ear canal 36 as necessary.

Figure 7:
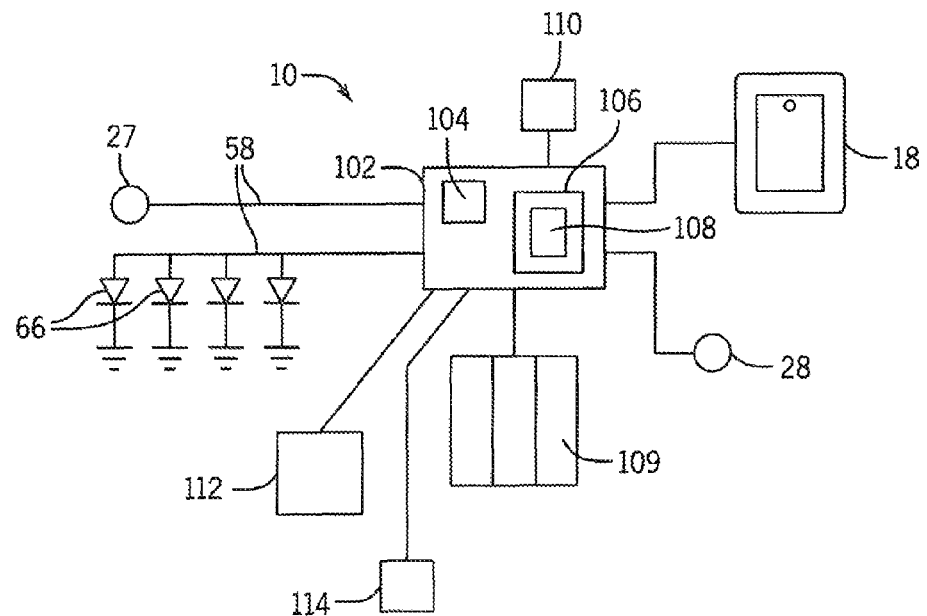
FIG. 7 is a simplified block diagram of the electronics of the otoscope of FIG. 1.

Referring now to FIG. 7, the otoscope 10 may incorporate an electronic controller 102 such as a microcontroller being in essence an electronic computer and I/O circuitry. The controller 102 will provide a processor 104 communicating with a memory 106 permitting non-transient storage of a program 108. Generally the program 108 will provide for the receipt of signals from the camera 27 and the display on display 18 of images from the camera. The program 108 may perform normal image processing, for example, exposure control, contrast adjustment, color balance and the like. The program 108 through the controller 102 may also control the illumination of the LEDs 66 as part of the exposure control process.

In some embodiments, the otoscope 10 may include an accelerometer 110 communicating with the microcontroller 120 to provide a signal indicating orientation of the grip portion 16 as may deviate from vertical. The signal may be used to rotate the image displayed on the display 18 instead of using knob 32 as described above to rotate the probe element 20, or may provide for a marker on the image denoting upward position.

The controller 102 may also communicate either through a wireless transceiver 112 or an electrical connector 114 with other devices such as a computer printer or the like so that images may be captured or transmitted as required by the camera 27.

The power button 28 may communicate with the controller 102 to put it into a low power sleep state, disabling the display 18, camera 27 and LEDs 66. The otoscope circuitry described above may be powered by a battery 109 contained in the housing 12.

Figure 8:
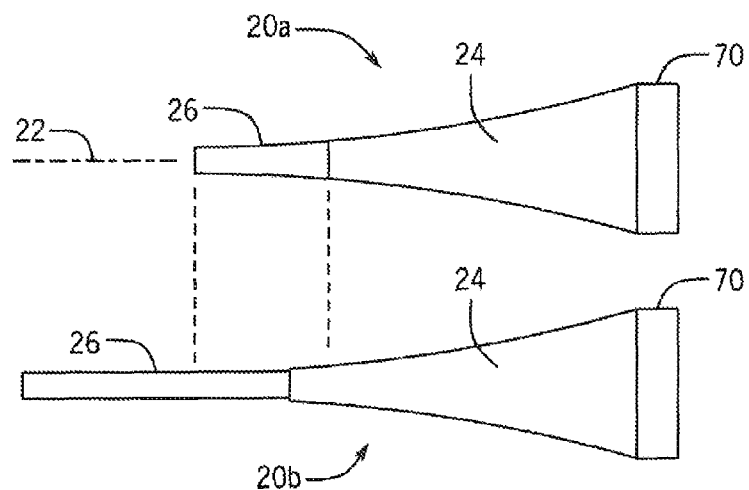
FIG. 8 is a side elevational view of multiple probe elements that may comprise a kit.

Referring now to FIG. 8, it will be appreciated that in the embodiment of FIG. 3, that multiple probe elements 20a and 20b may be provided for use in different applications, for example, for inspection of nasal cavities, the mouth, or throat, by simply changing a relative length of the probe element 20, and hence the distance it may pass through the ear or other cavity, and/or may change the relative length of the tip portion 26 or sheath 24 alone.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a controller" and "a processor" can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

"Diameter" as used herein should not be understood to require a cylindrical or circular element but to simply describe a diameter of a circumscribing cylinder closely conforming to the element.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

What we claim is:

1. An otoscope comprising:
   a housing providing a head portion and a grip portion, the grip portion adapted to be supported by a hand of a healthcare professional when the head portion is in an inspection position adjacent to an outer ear of an average patient;
   an elongate probe element having a proximal end supported by the head portion of the housing so that a distal end of the elongate probe element may extend along an axis into the ear canal of the outer ear in the inspection position; and
   an electronic camera supported by the elongate probe element for viewing into the ear canal when the distal end of the probe element is in the inspection position in the ear canal;
   wherein the elongate probe element is sized to be inserted into the ear canal for inspection of the ear canal without blocking the ear canal to access by other instruments within the ear canal and passing by the probe element as so inserted; and
   wherein the camera is positioned at a distal end of the elongate probe element and including conductors communicating between the distal end of the elongate probe element and a proximal end of the elongate probe element.

2. The otoscope of claim 1 wherein the elongate probe element includes a distal portion of maximum diameter less than an average diameter of the patient's ear canal for a length of at least one half the length of the patient's ear canal.

3. The otoscope of claim 2 wherein the maximum diameter is less than four millimeters.

4. The otoscope of claim 3 wherein the maximum diameter is less than 2.5 millimeters.

5. The otoscope of claim 2 wherein the length is at least one centimeter.

6. The otoscope of claim 5 wherein the distal portion of constant diameter has a length of at least two centimeters.

7. The otoscope of claim 1 wherein a distal portion of the elongate probe element is flexible to flex with contact against the ear canal.

8. The otoscope of claim 7 wherein the elongate probe element provides a flexure of a distal end at least one millimeter with an oblique force of less than 100 grams when the proximal end is stationary.

9. The otoscope of claim 7 wherein the elongate probe element provides a substantially rigid proximal portion providing less flexibility than the distal portion comprising at least one third a length of the elongate probe element.

10. The otoscope of claim 7 wherein the distal portion is a flexible member extending slidably and coaxially through a substantially rigid proximal portion.

11. The otoscope of claim 7 further including at least one LED supported at the distal end of the probe adjacent to the camera and directing light along the axis.

12. The otoscope of claim 1 further including a retraction mechanism for controlling an amount of extension and retraction of the elongate probe element along the axis with respect to the housing.

13. The otoscope of claim 1 wherein the elongate probe element includes a breakaway electrical connector connecting conductors within the elongate probe element to circuitry within the housing, the breakaway electrical conductor providing a reversible separation of connector portions at a predetermined oblique force.

14. The otoscope of claim 1 wherein the head portion includes at least one passageway extending substantially parallel to the axis to a side of the axis allowing insertion of tools through the head portion into the ear canal when the probe portion is within the ear canal.

15. The otoscope of claim 1 wherein the head portion supports the elongate probe element through a rotating coupling allowing rotation of the elongate probe element about the axis with respect to the head portion.

16. The otoscope of claim 1 wherein the grip portion extends substantially perpendicular to the axis of the probe.

17. The otoscope of claim 1 wherein the head portion includes an electronic display communicating with the camera portion for displaying an image from the camera.

18. The otoscope of claim 17 wherein the head portion includes at least one passageway extending substantially parallel to the axis to a side of the axis allowing insertion of tools through the head portion into the ear canal when the probe portion is within the ear canal and wherein the display is displaceably mounted on the housing to be moved from covering the passageway to uncovering the passageway.

19. The otoscope of claim 1 wherein housing holds a battery communicating electrical power to the camera.

* * * * *